(12) United States Patent
Brannon (10) Patent No.: US 6,872,184 B2
(45) Date of Patent: Mar. 29, 2005

(54) TISSUE COLLECTION APPARATUS

(76) Inventor: James Kevin Brannon, 5729 Canterbury Dr., Culver City, CA (US) 90230

( * ) Notice: Subject to any disclaimer, the term of this patent is extended or adjusted under 35 U.S.C. 154(b) by 482 days.

(21) Appl. No.: 09/865,339

(22) Filed: May 25, 2001

(65) Prior Publication Data

US 2002/0177785 A1 Nov. 28, 2002

(51) Int. Cl.$^7$ .............................................. A61B 10/00
(52) U.S. Cl. ...................................... 600/562; 600/300
(58) Field of Search ................................ 600/573, 562, 600/571, 300; 604/405, 406, 319

(56) References Cited

U.S. PATENT DOCUMENTS

| | | | | |
|---|---|---|---|---|
| 4,870,975 A | * | 10/1989 | Cronk et al. ................ | 128/749 |
| 4,957,492 A | * | 9/1990 | McVay ........................ | 604/319 |
| 5,108,381 A | * | 4/1992 | Kolozsi ....................... | 604/319 |
| 5,766,134 A | * | 6/1998 | Lisak et al. .................. | 600/562 |
| 5,779,649 A | * | 7/1998 | Herbert ....................... | 600/571 |
| 6,007,496 A | | 12/1999 | Brannon | |
| 6,083,175 A | * | 7/2000 | Lundgren .................... | 600/562 |
| 6,375,625 B1 | * | 4/2002 | French et al. ................ | 600/573 |
| 6,468,225 B1 | * | 10/2002 | Lundgren .................... | 600/562 |

OTHER PUBLICATIONS

Bone Graft Harvesting: A Percutaneous Technique, Salem, Michael, [BR] 1991; 73–B:867–8.

* cited by examiner

*Primary Examiner*—Henry Bennett
*Assistant Examiner*—Nihir B Patel (57) ABSTRACT

A tissue collection apparatus for initiating bone formation ex vivo. A substantially cylindrical body includes a closed end, an internal surface, an open proximal end and a detachable closure cap for preventing a flow of air at the juncture thereof and the substantially cylindrical body. A first portion is integral with the detachable closure cap for allowing a flow of a collection of bone growth elements substantially having a quantity of platelets, mesenchymal cells, bone cells, blood and tissue cells, collagen and noncollagenous proteins comprising components thereof to flow into the substantially cylindrical body and strike a procoagulant surface of an interpositional admixture element so as to induce aggregation and degranulation of the quantity of platelets. The interpositional element is interposed within the substantially cylindrical body. A second portion integral with the substantially cylindrical body is provided to allow the connection of vacuum means. The second portion includes a second internal passage to allow a flow of air there through.

16 Claims, 8 Drawing Sheets

TISSUE COLLECTION APPARATUS

BACKGROUND OF THE INVENTION

1. Field of the Invention

Bone grafting is among one of the most frequently performed surgical procedures by surgeons challenged with reconstructing or replacing skeletal defects. Over the years, several techniques have been devised to obtain and implant autologous bone. Scientist and clinicians have sought and defined the essential elements of bone healing and have further desired to secure these elements when considering the benefits of various types of bone grafting techniques. Recently, scientific inquiry has been directed toward understanding the role of bone morphogenic protein (BMP) in the process of new bone formation. What we have learned is that a simple fracture incites a tremendous cascade of events that lead to new bone formation, and that reducing this cascade to a product that can be sold is a difficult task if not impossible. Nonetheless, complex fractures continue to occur and are managed daily by orthopaedic surgeons. Therefore, if one is to appreciate the invention at hand the essentials of fracture healing and new bone formation must be understood.

The essential elements required for bone regeneration are osteoconduction, osteoinduction, and osteogenic cells. In this regard, autogenous bone is the gold standard for bone harvesting. Cancellous bone, as does cortical bone, contains all of these elements but lacks structural integrity. Cortical bone has structural integrity but is limited in quantity. At the histologic level, cortical bone is 4 times as dense as cancellous bone, and cancellous bone is 8 times as metabolically active as cortical bone. Further, clinicians have recognized the consequences of donor site morbidity and prolonged hospitalization after a traditional harvesting technique. To circumvent some of these issues, numerous synthetic bone like products have been made available for general use. Each product attempts to exploit one or more of the three essential elements of bone regeneration described above. Although many of these products, e.g., Pro Osteon, INTERPORE, Collagraft, ZIMMER, and others are unique, they remain expensive.

To define a less invasive technique for bone harvesting, percutaneous methods have been described. The recently developed techniques simply involve using a coring cylindrical device to obtain a segment of bone. David Billmire, M.D. describes this technique in his article, Use of the CORB Needle Biopsy for the Harvesting of Iliac Crest Bone Graft, PLASTIC AND RECONSTRUCTIVE SURGERY, February 1994. Billmire makes no effort to ensure the quality of the harvested bone but rather describes a power-driven counter-rotating hollow needle as cutting through bone and soft tissue. Michael Saleh describes a percutaneous technique for bone harvesting in his article, Bone Graft Harvesting: A percutaneous Technique, Journal of Bone and Joint Surgery [Br] 1991; 73-B: 867–8. The author describes using a trephine to twist and lever out a core of bone of 8 mm in size. Brannon, in U.S. Pat. No. 6,007,496, describes the use of a vacuum to create a pressure drop across an osteopiston of bone. Prior art fails to describe a method for performing bone grafting in situ.

When considering bone for grafting purposes, the recipient site must be considered as well. Failure to achieve bony union at a fracture site or bony fusion at a fusion site may be caused by several factors. Often, the blood flow is inadequate at the fracture site as a consequence of local trauma during the inciting event. Further, when considering augmentation of the healing process with bone graft, it is imperative that the grafted bone contains all of the essential elements germane to successful osseous regeneration, namely, osteoconductive elements, osteoinductive elements, and osteoprogenitor cells. Most current devices used for bone grafting focus on quantity, the osteoconductive portion of the harvested bone, and less so on quality, the osteoinductive portion of the harvested bone. Recently, bone substitutes have been developed and can be classified according to the following major categories: 1) Osteoconductive synthetics (Pro Osteon 500), 2) Osteoinductive allograft (Grafton), 3) Osteoinductive biosynthetics (OP-1), 4) Osteoinductive autologous bone marrow aspirates, 5) Osteoconductive/Osteoinductive combination synthetics, and 6) Gene therapy. When implanting the above bone graft substitues, recognizing the usefulness of a collection of bone growth elements at the fracture site or those generated during the process of open reduction and internal fixation (ORIF) or any other bony procedure, such as posterior spinal instrumentation, has not been achieved through the development of a simple device to promote in situ bone grafting. In this regard, synthetic alternatives to bone grafting can be used as expanders that can be added to autogenous bone and mesenchymal cells harvested in situ at the fracture site or the surgical site. This approach will indeed ensure that all patients are given an optimal opportunity for bony union or bony fusion.

2. Information Disclosure Statement

To recognize the issues at hand governing the invention described herein, a simple discussion of biomechanics, physiology, and some general physics is warranted and presented in support hereof.

Bone is a viscoelastic material, and as such, it behaves predictably along its stress strain curve when axially loaded in either tension or compression. The key word here is viscoelastic. The prefix "visco" describes the fluid component of the material being tested and the suffix "elastic" describes the recoil potential of the material being tested. The ratio of stress:strain is Young's Modulus. Clearly, a spring is fully elastic. One may place a tension force on a spring, but when the tension is released, the spring recoils to its original length. A syringe, on the other hand, with a thin hypodermic needle attached, is considered viscoelastic. In other words, the amount of deformation observed is time dependent. Simply, the deformation will remain after the tension is removed. Consider one throwing Silly Putty against the ground and observing it bounce versus letting the material sit on a counter for several hours. One should appreciate that minimal deformation occurs when the Silly Putty bounces from the floor versus sitting it on a counter for several hours. The deformation is time dependent as a consequence of the internal fluid properties of the material; an amount of time is required to observe a net fluid flow. Bone behaves in a similar fashion, but has the additional property of being able to respond to a given stress by forming new bone. When bone fails to respond favorably, it fractures.

The physiologic properties of bone hinge on the fluid elements that govern bone regeneration, namely, bone morphogenic protein, various hormones, and osteoprogenitor cells. These fluid elements are integral to the physiologic function of bone and are found within the bone marrow and the circulatory system. Appreciate that there is a net flow of these elements as bone bares a daily physiologic load during normal walking. Since the circulatory system is a closed system, a net loss of these fluid elements is not observed but rather continuous remodeling of bone and metabolic maintenance of the various cells and proteins as they age and become nonfunctional.

Bone is incompressible above or below its elastic limit, i.e., Young's Modulus. Poisson's ratio is used to describe this behavior and can be defined as follows:

$$v = -(\Delta d/d_0)/(\Delta l/l_0) \quad (1),$$

Poisson's ratio can be thought of as a measure of how much a material thins when it is stretched, consider taffy, or how much a material bulges when it is compressed. Regarding bone, one does not necessarily observe an increase in volume when it is compressed, but rather an increase in the density as bone remodels along the lines of stress, i.e., form follows function, Wolff's Law. When bone is compressed beyond its elastic limit, it fractures, therefore, its area will increase in a direction perpendicular to the line of force. The fracture observed occurs in the osteoconductive portion of bone, and a fluid flow will occur, as a result of the fracture, within the osteoinductive portion of bone.

The physiology of bone form and function is clear, but what a physician may observe through a series of x-rays may vary from patient to patient. Clearly then what we look for on a x-ray is evidence of healing, and in this regard, fracture healing is divided into at east four categories as follows: 1) Inflammatory stage, 2) Soft callus stage, 3) Hard callus stage, and 4) Remodeling stage. Each of these stages have clinical parameters that can be evaluated at the bedside. It is important to note, however, that any healing process in the human begins with clot formation; consider a simple laceration. Thus, fracture healing begins with clot formation. However, this stage of fracture healing does not have a clinical parameter unless the fracture is considered an open fracture.

The continues fluid nature of whole blood (formed elements, i.e., blood cells; serine proteases, i.e., clotting factors; proteins, carbohydrates, electrolytes and hormones) while circulating in the vascular system is substantially maintained by the endothelial lining along the vessel walls. When these circulating serine proteases are exposed to subendothelial collagen or surfaces other than endothelial cells, i.e., abnormal surfaces, platelets aggregate and the clotting cascade is initiated. Blood without formed elements is considered plasma, while plasma without clotting factors is considered serum. A collection of autogenous bone growth elements is considered any and all factors germane to bone formation.

The clotting cascade is divided into two arms; the intrinsic pathway, i.e., local tissue trauma incites clot formation through exposure of the subendothelial collagen to circulating serine proteases and platelets; and the extrinsic pathway which incites clot formation through the activation of Factor VII serine protease and by tissue thromboplastin released from damaged cells. Both pathways then converge on Factor X serine protease. Regarding platelets, these cells are first to arrive and become adherent to injured tissue and form a platelet plug. Adherent platelets are activated platelets and as such release hemostatic agonist and autologous growth factors through a process of degranulation. The hemostatic agonist promotes clot formation to ensure that the bleeding stops, while the autologous growth factors initiate the healing process of the injured tissue. Unique to bone is its healing process is more regenerative of new bone formation as opposed to reparative which is more indicative of scar formation. Scar formation in fracture healing is a nonunion. Further, when bone fractures as a result of surgical or unintentional trauma, a collection of bone growth elements are generated directly within the fracture that contain both fluid and non-fluid components. Within the fluid component are platelets, blood and bone marrow mesenchymal cells, collagen and noncollagenous proteins, and small spickules of bone. The solid component is considered the bony fragments. ORIF is specifically designed to restore length and alignment of the fractured bone through rigid fixation of the non-fluid component. Bone grafting is used when it is determined preoperatively that the structural integrity and the quantity of the bony fragments are insufficient to allow ORIF. Clearly, the collection of bone growth elements required for bony union is present at the fracture site at the time of surgical or unintentional trauma. It stands to reason that in situ autologous bone growth elements, fluid and non-fluid, should be retained and used in conjunction with ORIF or bone graft expanders so as to improve patient outcomes. In situ autologous bone growth factors at a given fracture site unequivocally include the appropriate level of BMPs and other noncollagenous proteins at the various stages of fracture healing as described above. The isolation and/or recombinant synthesis of bone growth factor and their subsequent injection into a nonunion makes the assumption that the given fracture failed to heal because the collection of bone growth elements present in the initial fracture lacked the specific growth factor being injected or a sufficient quantity of the same. Further, one must also assume that the receptor cells for the growth factors are present at the nonunion and simply lack stimulation by the growth factor being injected. Again, autologous bone is the gold standard by which all bone replacement alternatives are compared. Understanding the physiology of new bone formation, a reparative process, will lend credence to how one should collect and use bone graft elements harvested in situ or from a second operative site. The invention described herein uniquely exploits the above principles so as to ensure the optimum chance for bony union or bony fusion.

SUMMARY AND OBJECTS OF THE PRESENT INVENTION

It is an object of the present invention to provide a method for collecting fluid autogenous bone growth elements in situ.

It is yet a further object of the present invention to provide means for initiating new bone formation ex vivo within a collection of fluid autogenous bone growth elements.

It is yet a further object of the present invention to ensure that the harvested fluid autogenous bone growth elements retain all of the essential components deemed necessary for new bone formation.

It is yet a further object of the present invention to substantially retain and collect morrow mesenchymal cells present at a given fracture site.

It is yet a further object of the present invention to promote all musculoskeletal surgeons to use autogenous bone in situ when bone grafting is required for new bone formation.

SUMMARY

The invention describes a novel and unobvious method for collecting the fluid component of autogenous bone growth elements generated at a fracture site. The bone growth elements can be generated either intentionally, i.e., surgery, or unintentionally, i.e., accidental trauma. An inlet connection tube may have a rigid extension for inserting into a fracture hematoma. The inlet connection tube communicates with a substantially cylindrical body in which is housed an interpositional admixture element or ex vivo interpositional platelet aggregating membrane for promoting platelet aggregation, clot formation and the initiation of new bone formation. The element for promoting clot formation comprises means for a volumetric increase in a quantity of clot and further induces platelet degranulation. The clot-promoting element is of a size and dimension to ensure at all times a path of least resistance for the continuous flow of air through the cylindrical body. The collection of bone growth elements are then removed from the substantially cylindrical body and implanted into the fracture site.

DESCRIPTION OF THE PREFERRED EMBODIMENTS

Figure 1:
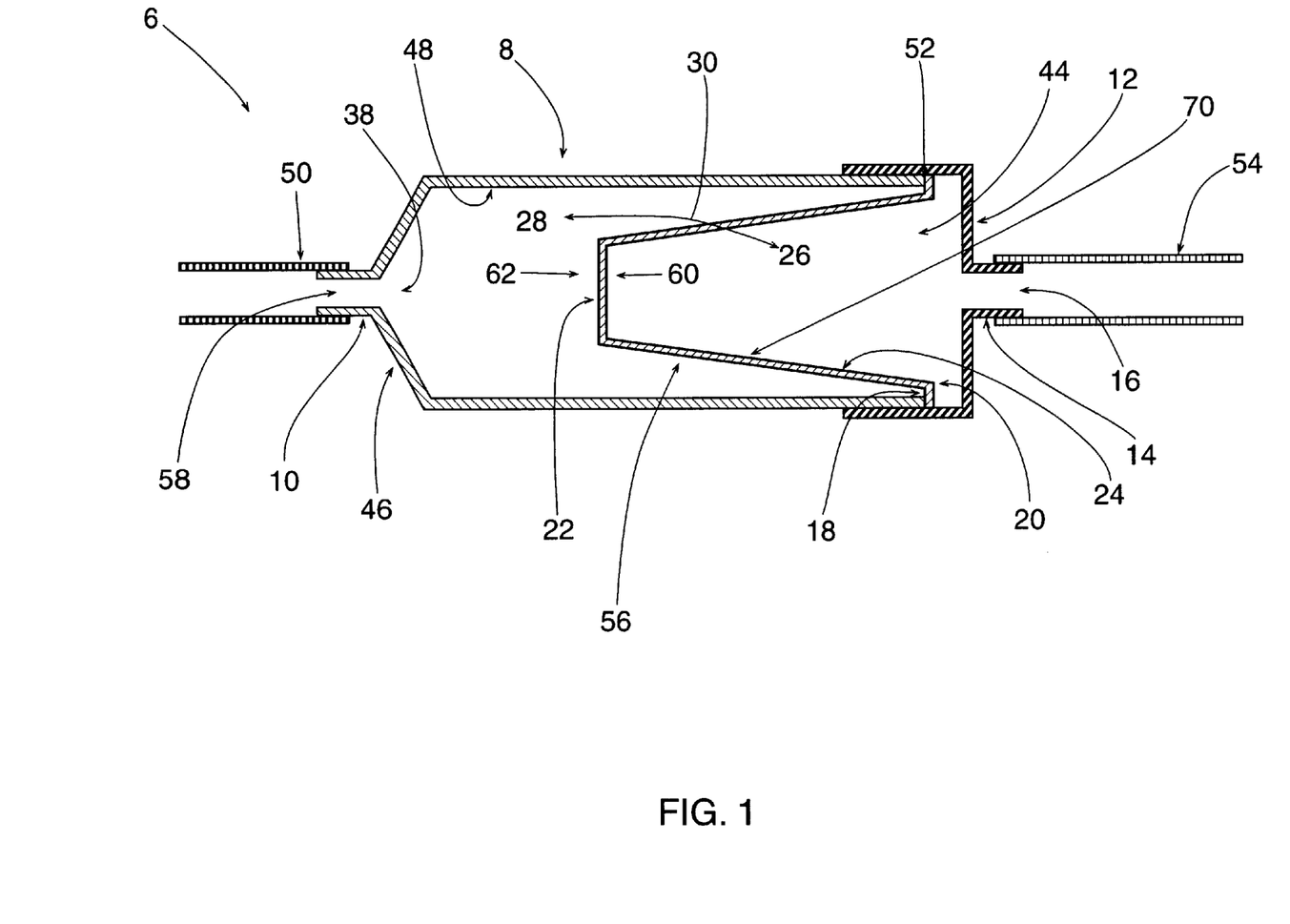
FIG. 1 is a sectional view of the cylinder, the interpositional admixture element without a collection of autogenous bone growth elements.

There shown generally at 6 in FIG. 1 is a substantially cylindrical body 8 having an open proximal end 44 and a closed distal end 46 having a partial opening 38 and a second portion 10 extending away from the partial opening. The cylindrical body 8 includes an internal surface 48 and a proximal surface 52. In operational relationship therewith the substantially cylindrical body 8 is a detachable closure cap 12 for hermetically sealing the open proximal end 44 so as to prevent the retrograde flow of air at the juncture thereof and the detachable closure cap 12. The detachable closure cap 12 includes a first portion 14 having a first internal passage 16 for purposes of allowing a fluid to flow therethrough. An interpositional admixture element 56 having a proximal facing tissue surface 60 and a distal facing chamber surface 62 is interposed therebetween the detachable closure cap 12 and the closed distal end 46 so as to establish a tissue chamber 26 proximally and an air chamber 28 distally. The first portion 14 is further of a size and shape adapted to receive a first connection tube 54. The second portion 10 is of a size and shaped adapted to receive a second connection tube 50 and further includes a second internal passage 58 for allowing air to flow therethrough. The interpositional admixture element 56 includes a distal portion 22 adapted to receive a collection of bone growth elements 36 and further includes a proximal extent 20. The components of the collection of bone growth elements 36 can principally include a quantity of platelets, mesenchymal cells, bone cells, blood and tissue cells, collagen and noncollagenous proteins.

Figure 2:
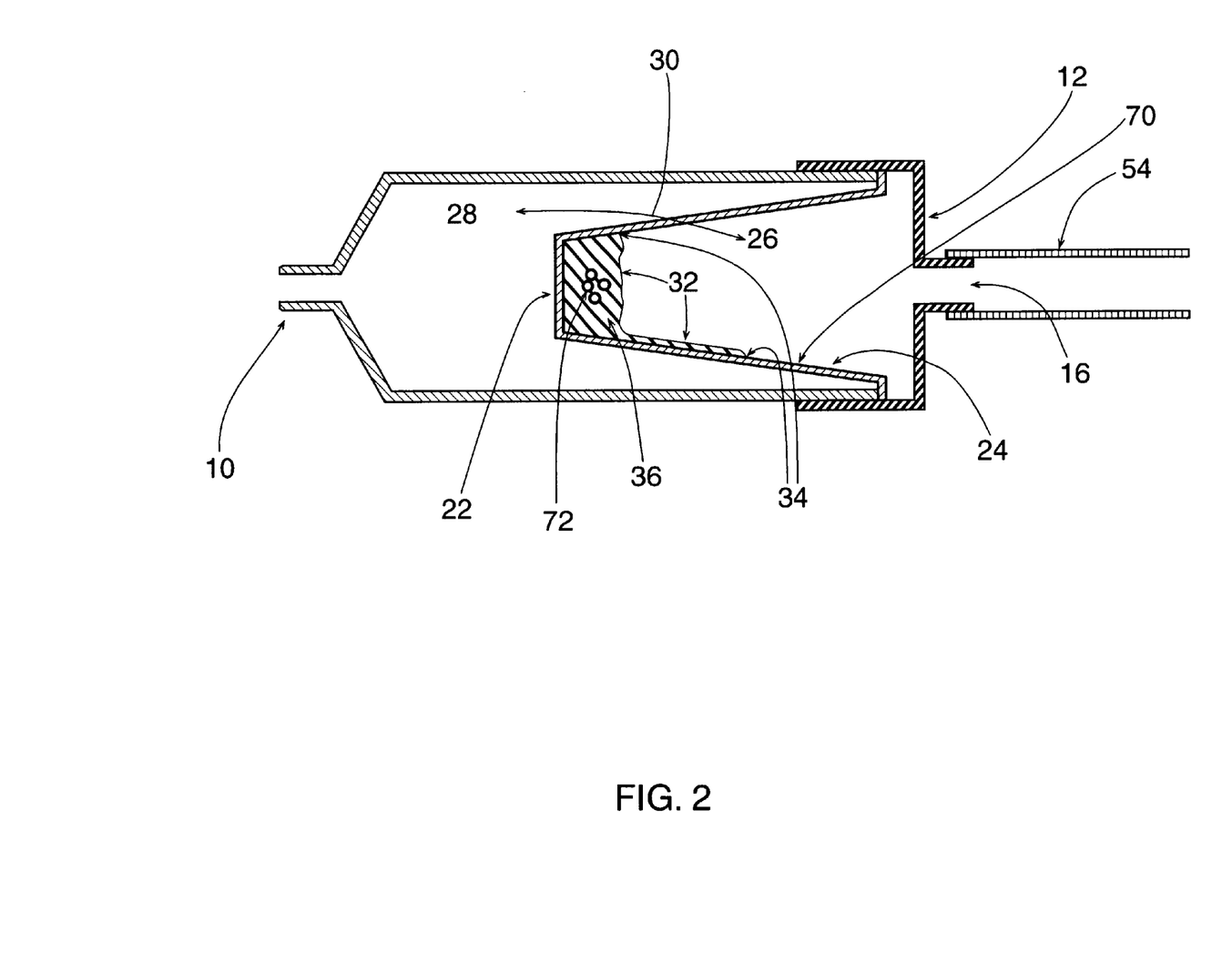
FIG. 2 is a sectional view of the cylinder, the interpositional admixture element with a collection of autogenous bone growth elements.
Figure 3:
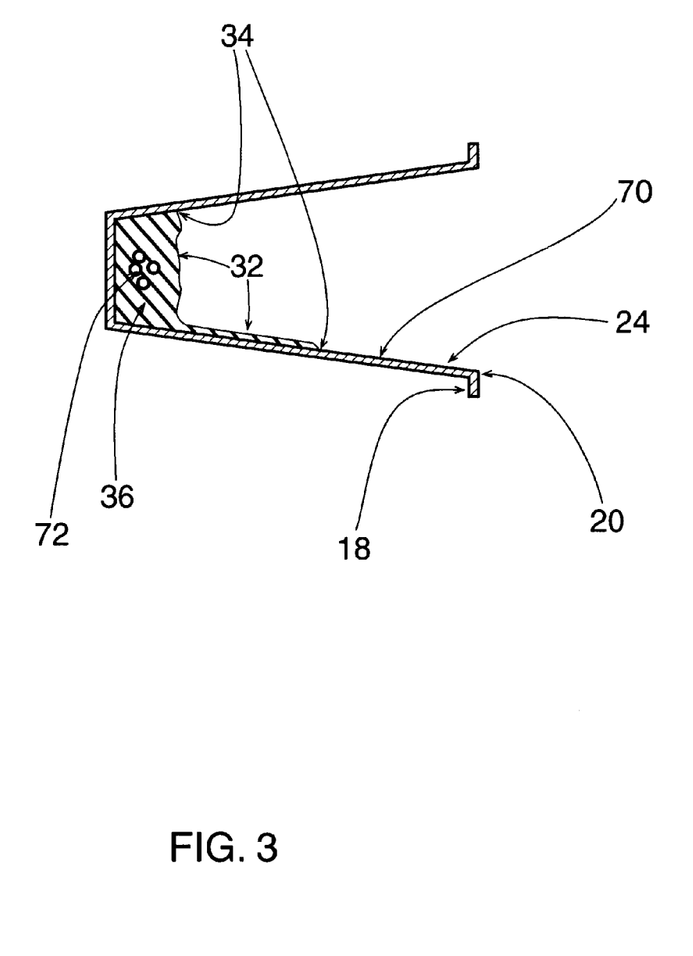
FIG. 3 is a sectional view of the interpositional admixture element with a collection of autogenous bone growth elements.

Now turning to FIGS. 2 and 3, the device of this invention is shown. The interpositional admixture element 56 having the distal portion 22 has received the collection of bone growth elements 36. The collection of bone growth elements has a tissue surface 32 and a peripheral margin 34. The peripheral margin 34 of the collection of bone growth elements 36 defines a peripheral portion 24 of the interpositional admixture element 56 at the juncture thereof and extends proximally to the proximal extent 20. The peripheral portion 24 of the interpositional admixture element 56 has a surface plane 64. The interpositional admixture element 56 is of a size and dimension to ensure that the collection of bone growth elements 36 strike an area of contact or a procoagulant surface 70 within the peripheral portion 24.

Figure 4:
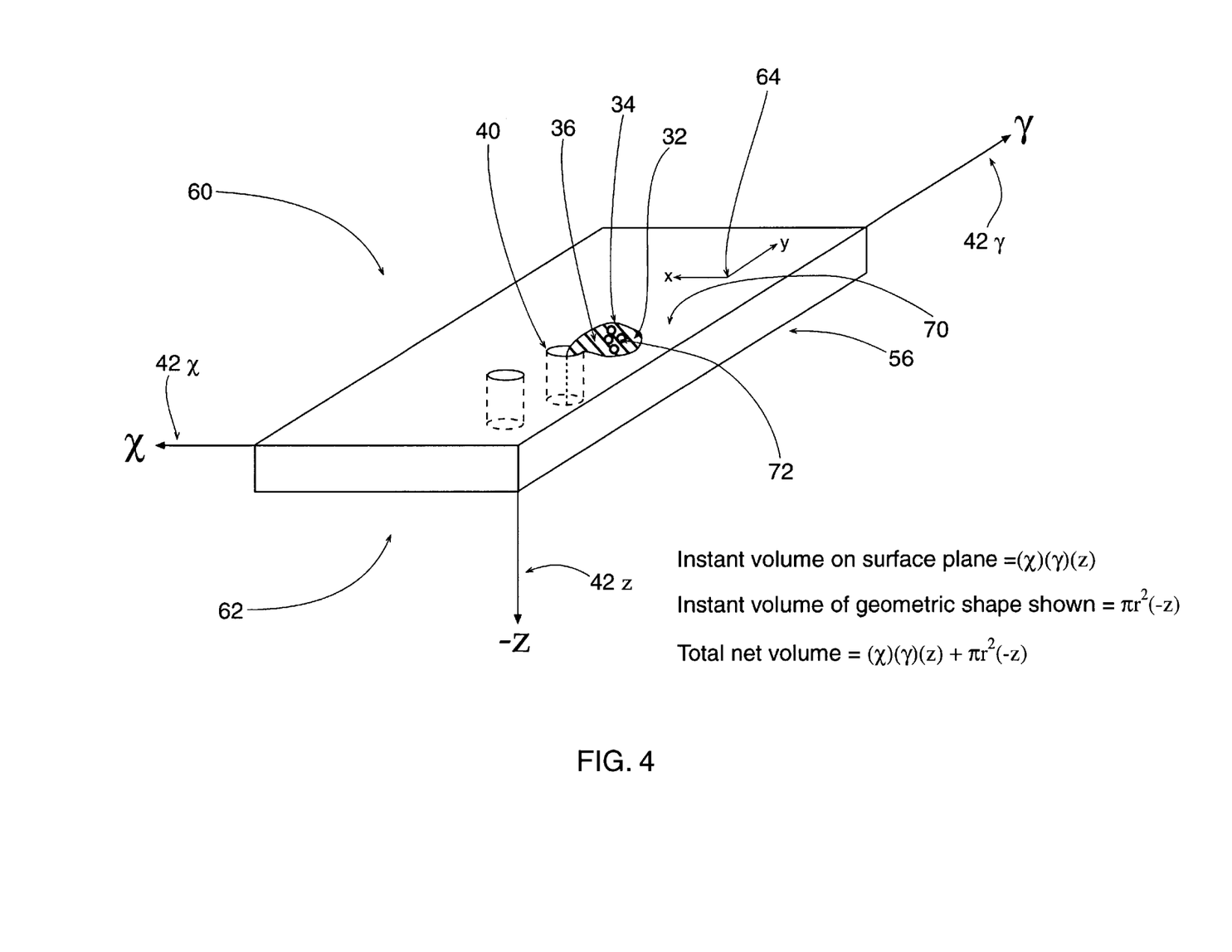
FIG. 4 is an expanded sectional view of the interpositional admixture element with a collection of autogenous bone growth elements showing the orthogonal planes of reference for a volumetric increase in clot formation.

Now turning to FIG. 4, the device of this invention is further shown. The interpositional admixture element 56 includes a plurality of surface gaps 40 or a plurality of surface incontinuities. The surface gaps 40 are generally shown as circular in configuration, however, such configuration has no influence on their purpose and function described herein, as these surface gaps 40 can be any configuration and are distributed throughout the distal portion 22 and the peripheral portion 24. The surface gaps 40 ensure a passageway between the proximal facing tissue surface 60 and the distal facing chamber surface 62. The interpositional admixture element having surface gaps or surface incontinuities functionally serves as a subendothelial like substrate to which platelets aggregate ex vivo. Platelet aggregation induces clot formation and platelet degranulation. The degranulation of platelets is principally the release of cell mediators and homeostatic agonist from subcellular granules within the platelets. The cell mediators include autologous growth factors, inflammatory and hemostatic agonist. More specifically, autologous growth factors induce mesenchymal cell differentiation into a collection of the constitutive cells of the injured tissue. Noncollagenous proteins in the case of bone, specifically BMPs, help direct mesenchymal cells stimulated by platelet derived autologous growth factors to differentiate into bone forming cells. The interpositional admixture element ensures that the mesenchymal cells are exposed to a sufficient quantity of autologous growth factors to initiate bone formation ex vivo. This mesenchymal cells exposure is achieved by inducing platelet aggregation along the surface plane 64 having the area of contact or procoagulant surface 70 and within the surface gaps 40. The surface gaps 40 have a dual function in that they first promote platelet aggregation thereby inducing clot formation and platelet degranulation and consequentially inducing new bone formation ex vivo within the collection of bone growth elements 36 and second the surface gaps 40 establish and ensure at all times a passageway therethrough the interpositional admixture element 56. In operational combination the tissue chamber 26, the surface gaps 40, and the air chamber 28 comprise a vacuum path of least resistance 30. However, the vacuum path of least resistance may include the tissue chamber 26 alone or the tissue chamber and the air chamber 28 in combination. The shape and dimension of the interpositional admixture element 56 ensures at all times a gravitational flow of the collection of bone growth elements 36 along the surface plane 64. The gravitational flow is of a magnitude to induce mixing of components of the collection of bone growth elements flowing thereon the surface plane 64. The gravitational flow is further of a magnitude to induce platelet adhesion and platelet aggregation along the surface plane 64. The platelet adhesion is of a degree to substantially retain the platelets within the collection of bone growth elements. FIG. 4 further shows that in an instant moment the collection of bone growth elements 56 lies substantially along the surface plane 64 in an x orthogonal axis 42x and a y orthogonal axis 42y. The net sum of a volumetric increase in a quantity of clot 72 within the collection of bone growth elements 56 is realized through the sum of a first instant volume of the collection of bone growth elements along the surface plane 64 and the sum of a second instant volume of the collection of bone growth elements within the surface gaps 40 parallel to a z orthogonal axis 42z. Further, the net sum of the volumetric increase in the quantity of clot 72 within orthogonal axes 42x, 42y, and 42z in any instant is greater than a given volume of clot within orthogonal axes 42x and 42y alone and thereby substantially potentiates new bone formation ex vivo. The interpositional admixture element 56 includes a securing member or geometric body 18 for detachably and circumferentially engaging the proximal surface 52. The securing member or geometric body 18 is of a size and dimension adapted to allow the retrieval of the bone growth elements collected therein.

Figure 5:
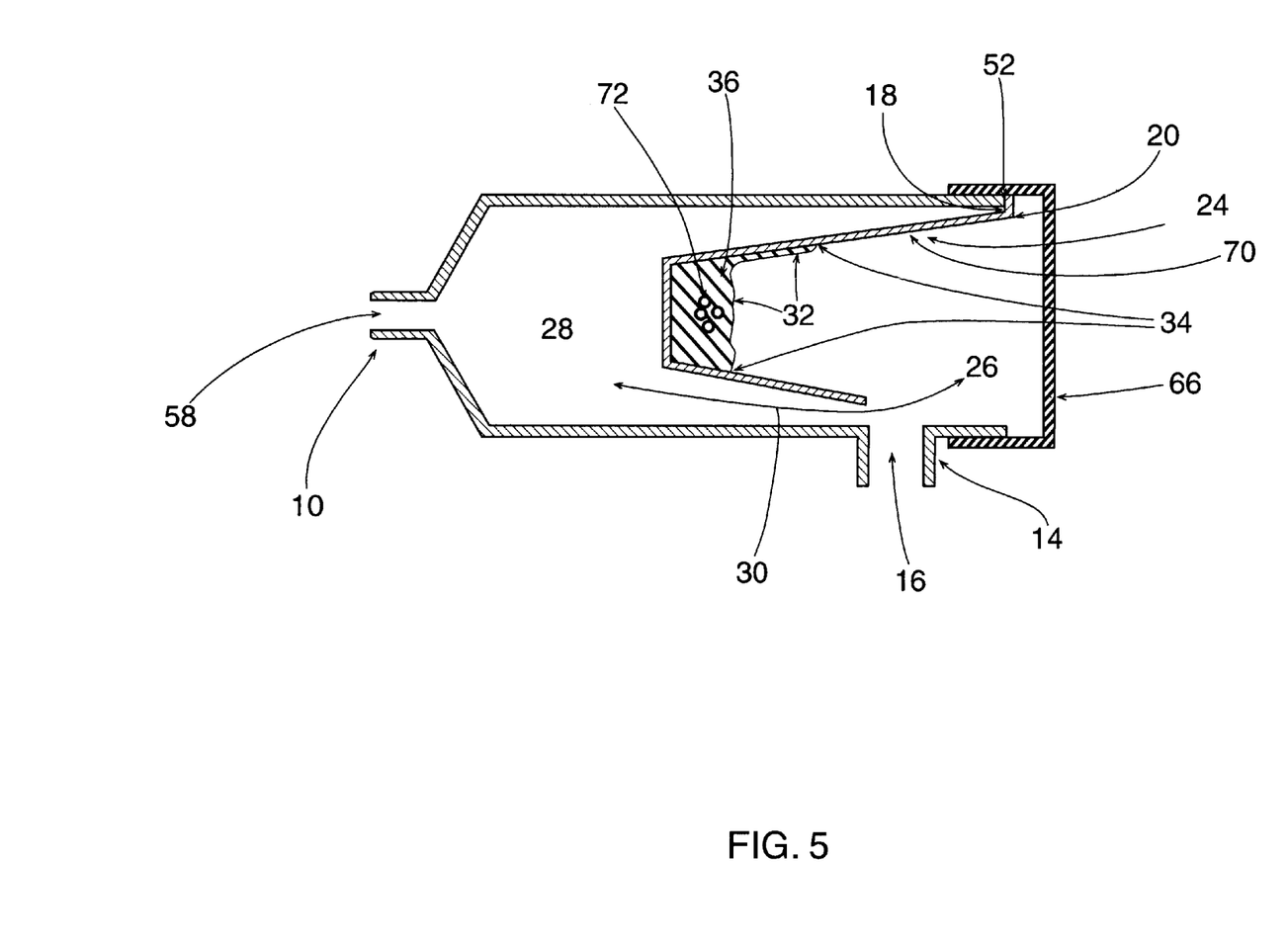
FIGS. 5, 6, 7 and 8 are alternative embodiments of the invention described herein.

Now turning to FIG. 5, an alternative embodiment of the invention is shown wherein the substantially cylindrical body 8 includes the first portion 14 having the first internal passage 16 integral therewith. The substantially cylindrical body further includes the second portion 10 having the second internal passage 58 as shown in FIG. 1. A detachable cap 66 operationally engages the open proximal end 44 so as to prevent the retrograde flow of air at the juncture thereof and the detachable cap 66. The interpositional admixture element 56 is operationally interposed therebetween the first portion 14 and the second portion 10 so as to ensure that the proximal facing tissue surface 60 faces the first portion 14 and the distal facing chamber surface 62 faces the second portion 10.

Figure 6:
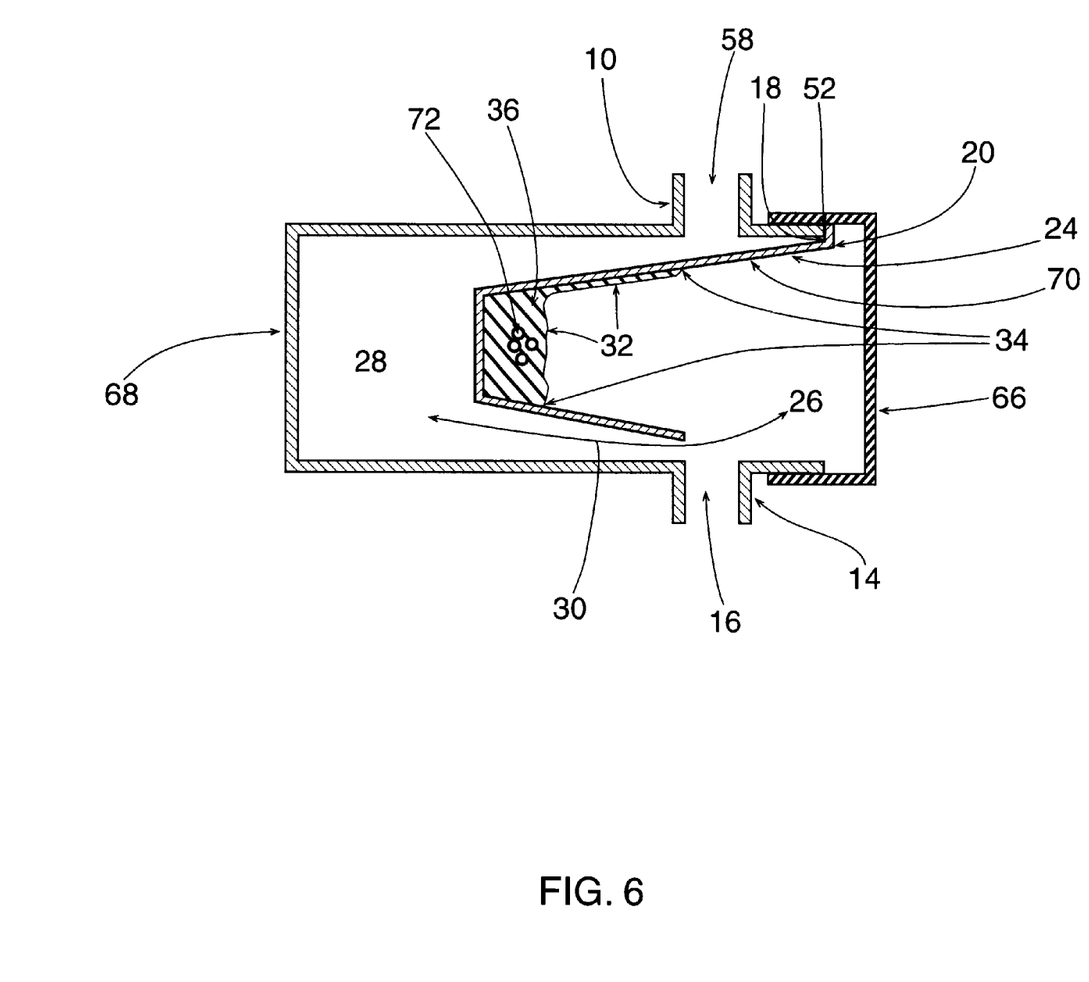

Now turning to FIG. 6, yet another alternative embodiment of the invention is shown. Integral therewith, the substantially cylindrical body 8 includes the first portion 14 having the first internal passage 16 and a second portion 10 having a second internal passage 58. The substantially cylindrical body 8 further includes a closed end 68. The detachable cap 66 operationally engages the open proximal end 44 so as to prevent the retrograde flow of air at the juncture thereof and the detachable cap 66. The interpositional admixture element 56 is operationally interposed therebetween the first portion 14 and the second portion 10 so as to ensure that the proximal facing tissue surface 60 faces the first portion 14 and the distal facing chamber surface 62 faces the second portion 10.

Figure 7:
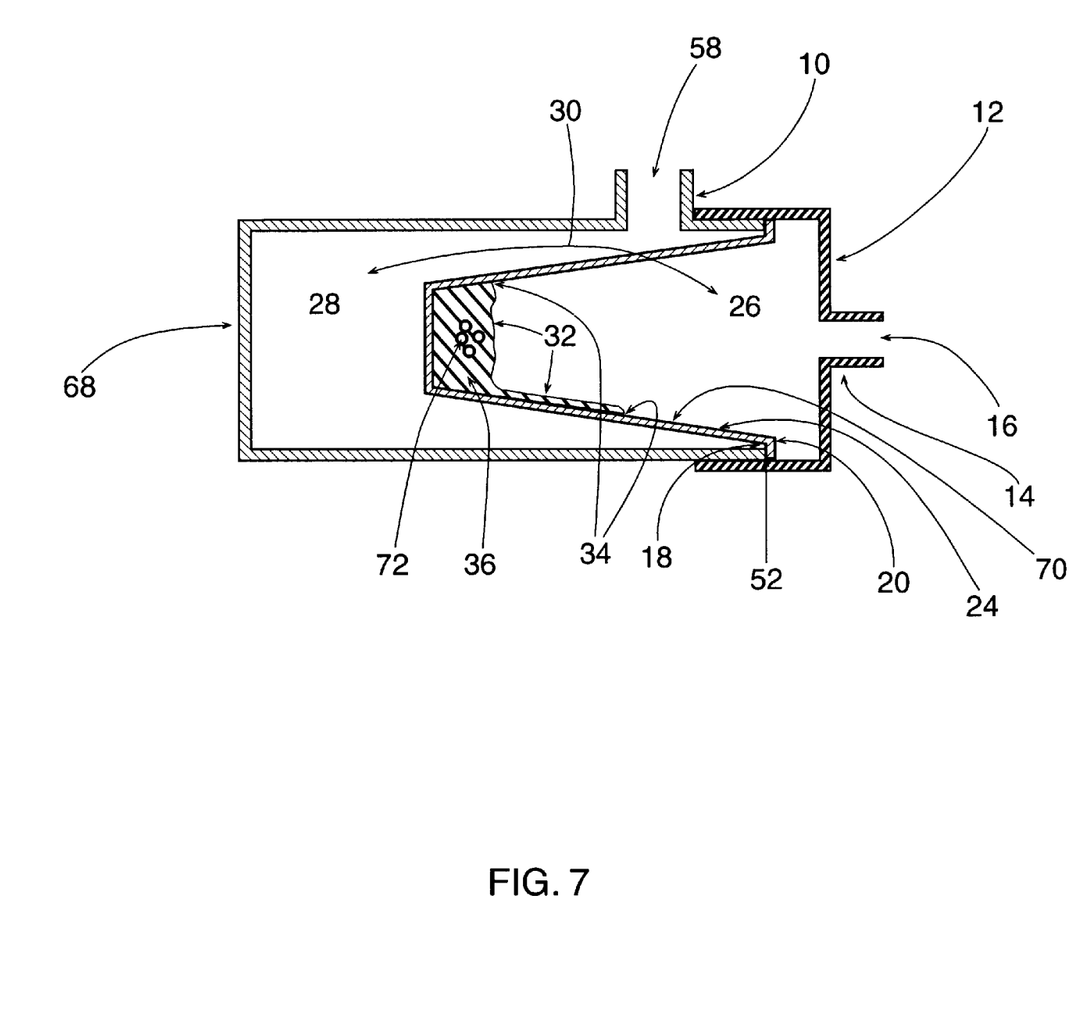

Now turning to FIG. 7, yet another alternative embodiment of the invention is shown. Integral therewith, the substantially cylindrical body 8 includes a second portion 10 having a second internal passage 58 and a closed end 68. In operational relationship therewith the substantially cylindrical body 8 further includes a detachable closure cap 12 for hermetically sealing the open proximal end 44 so as to prevent the retrograde flow of air at the juncture thereof and the detachable closure cap 12. The detachable closure cap 12 includes a first portion 14 having a first internal passage 16 for purposes of allowing a fluid to flow therethrough. The interpositional admixture element 56 is operationally interposed therebetween the first portion 14 and the second portion 10 so as to ensure that the proximal facing tissue surface 60 faces the first portion 14 and the distal facing chamber surface 62 faces the second portion 10.

Figure 8:
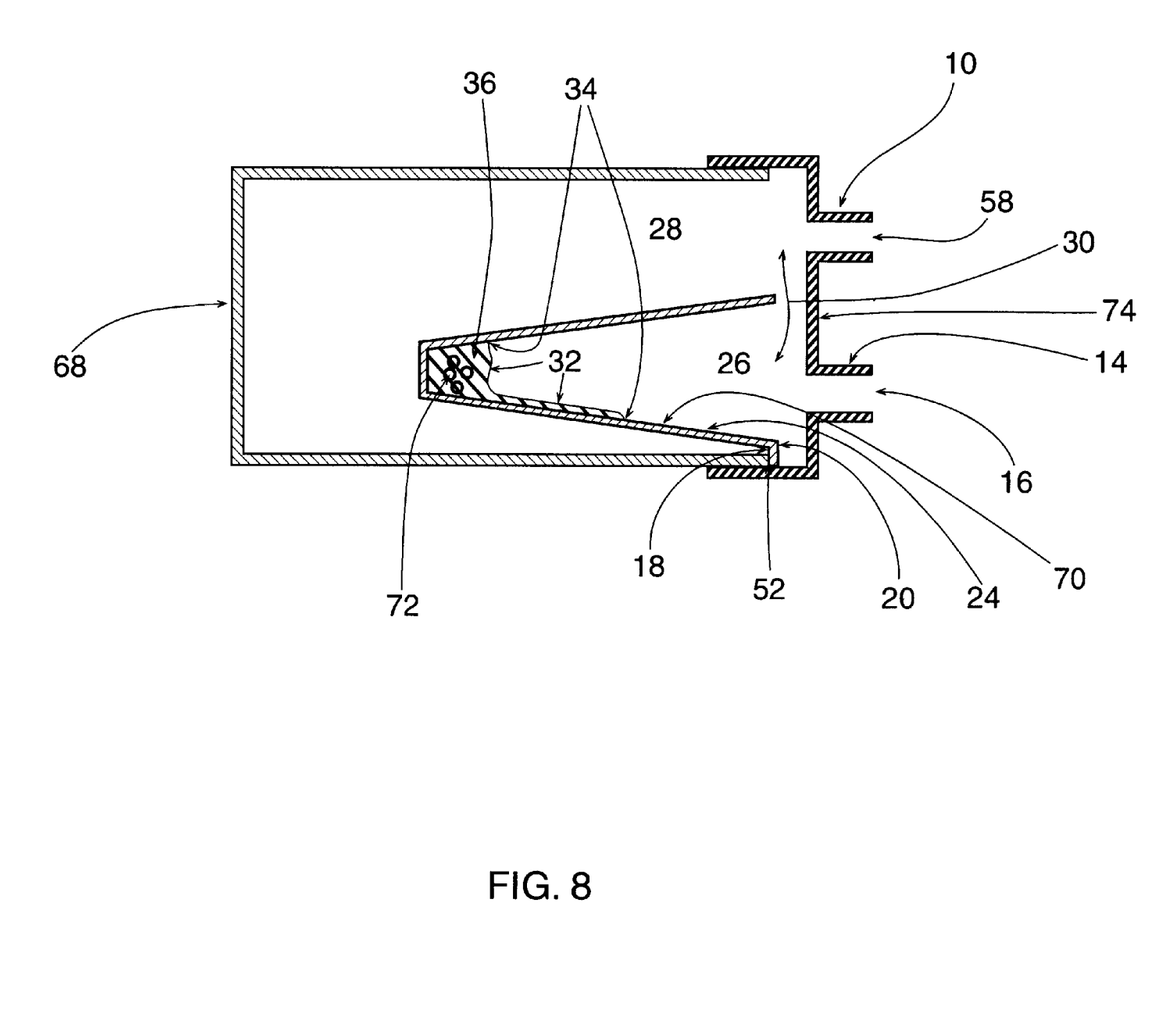

Now turning to FIG. 8, yet another alternative embodiment of the invention is shown. In operational relationship therewith the substantially cylindrical body 8 further includes a detachable sealing cap 74 for hermetically sealing the open proximal end 44 so as to prevent the retrograde flow of air at the juncture thereof and the detachable sealing cap 74. The detachable sealing cap 74 includes a first portion 14 having a first internal passage 16 for purposes of allowing a fluid to flow therethrough and a second portion 10 having a second internal passage 58 for allowing air to flow therethrough. The interpositional admixture element 56 is operationally interposed therebetween the first portion 14 and the second portion 10.

The invention at hand is a very unique way of collecting and transplanting in situ a collection of bone growth elements at a fracture site, and further promotes new bone formation ex vivo. What has been described is illustrative only and by no means is intended to represent all embodiments or modifications, as one might conceive an alternative embodiment, but such alternative embodiment would not deviate from the spirit of the invention.

Thus having described the invention, what I desire to claim and secure by Letters Patent is:

1. A tissue collection apparatus comprising:
   a substantially cylindrical body having an open proximal end, an internal surface, a proximal surface and a closed end, said substantially cylindrical body further includes a detachable closure cap having a first portion of a size and shape adapted to receive a first connection tube, said detachable closure cap is of a shape and dimension to seal hermetically said open proximal end so as to prevent the flow of air at the juncture thereof and said substantially cylindrical body, said first portion includes a first internal passage for allowing a collection of bone growth elements substantially having platelets, mesenchymal cells, bone cells, blood and tissue cells, collagen and noncollagenous proteins comprising components thereof to flow through said first connection tube, said first internal passage and into said substantially cylindrical body, the collection of bone growth elements includes a proximal tissue surface and a peripheral tissue margin;
   an interpositional admixture element having a proximal extent and a distal portion adapted to receive the collection of bone growth elements and define a peripheral portion at the juncture thereof and said proximal extent, said interpositional admixture element includes a proximal facing tissue surface and a distal facing chamber surface, said interpositional admixture element further includes means for initiating bone formation therewithin the collection of bone growth elements, said means comprising a plurality of surface gaps having a size adapted to induce clot formation therewithin the collection of bone growth elements, said plurality of surface gaps ensure a passageway therebetween said proximal facing tissue surface and said distal facing chamber surface of said interpositional admixture element, said interpositional admixture element is operationally interposed therebetween said detachable closure cap, said internal surface and said closed end so as to ensure that the collection of bone growth elements strike an area of contact along a surface plane of said peripheral portion, said interpositional admixture element is further interposed so as to establish a tissue chamber proximally and an air chamber distally within said substantially cylindrical body, said interpositional admixture element is of a shape and dimension to ensure at all times a vacuum path of least resistance, said vacuum path of least resistance comprising said tissue chamber, said plurality of surface gaps throughout said peripheral portion and said air chamber, said interpositional admixture element is further of a size and dimension so as to induce a gravitational flow of the collection of bone growth elements along said surface plane, the gravitational flow is of a magnitude to induce mixing of components of the collection of bone growth elements; and
   a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

2. A tissue collection apparatus as described in claim 1 wherein said proximal extent further includes a securing member in operational relationship therewith for detachably engaging said proximal surface.

3. A tissue collection apparatus comprising:
   a substantially cylindrical body having an open proximal end, an internal surface, a proximal surface and a closed distal end, said substantially cylindrical body further includes a detachable closure cap having a first portion of a size and shape adapted to receive a first connection tube, said detachable closure cap is of a shape and dimension to seal hermetically said open proximal end so as to prevent the flow of air at the jucture thereof and said substantially cylindrical body, said first portion includes a first internal passage for allowing a collection of bone growth elements substantially having platelets, mesenchymal cells, bone cells, blood and tissue cells collagen and noncollagenous protein comprising components thereof to flow through said first connection tube, said first internal passage and into said substantially cylindrical body, the collection of bone growth elements includes a proximal tissue surface and a peripheral tissue margin;

an interpositional admixture element having a proximal extent and a distal portion adapted to receive the collection of bone growth elements and define a peripheral portion at the juncture thereof and said proximal extent, said interpositional admixture element includes a proximal facing tissue surface and a distal facing chamber surface, said interpositional admixture element further includes means for initiating bone formation therewithin the collection of bone growth elements, said means comprising a plurality of surface gaps having a size adapted to induce clot formation therewithin the collection of bone growth elements, said plurality of surface gaps ensure a passageway therebetween said proximal facing tissue surface and said distal facing chamber surface of said interpositional admixture element, said interpositional admixture element is operationally interposed therebetween said detachable closure cap, said internal surface and said closed distal end so as to ensure that the collection of bone growth elements strike an area of contact along a surface plane of said peripheral portion, said interpositional admixture element is further interposed so as to establish a tissue chamber proximally and an air chamber distally within said substantially cylindrical body, said interpositional admixture element is of a shape and dimension to ensure a vacuum path of least resistance, said interpositional admixture element is further of a size and dimension so as to induce a gravitational flow of the collection of bone growth elements along said surface plane, the gravitational flow is of a magnitude to induce mixing of components of the collection of bone growth elements; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

4. A tissue collection apparatus as described in claim 3 wherein said proximal extent further includes a securing member in operational relationship therewith for detachably engaging said proximal surface.

5. A tissue collection apparatus comprising:

a substantially cylindrical body having an open proximal end, an internal surface, a proximal surface and a closed distal end, said substantially cylindrical body further includes a detachable closure cap having a first portion of a size and shape adapted to receive a first connection tube, said detachable closure cap is of a shape and dimension to seal hermetically said open proximal end so as to prevent the retrograde flow of air at the juncture thereof and said substantially cylindrical body, said first portion includes a first internal passage for allowing a collection of bone growth elements substantially having platelets, mesenchymal cells, bone cells, blood and tissue cells, collagen and noncollagenous proteins comprising components thereof to flow through said first connection tube, said first internal passage and into said substantially cylindrical body, the collection of bone growth elements includes a proximal tissue surface and a peripheral tissue margin;

ex vivo bone forming surface means for initiating bone formation within the collection of bone growth elements, said ex vivo bone forming surface means comprising an interpositional admixture element having a plurality of surface gaps of a dimension adapted to induce clot formation volumetrically, said interpositional admixture element includes a proximal extent and a distal portion adapted to receive the collection of bone growth elements and define a perpheral portion at the jucture thereof and said proximal extent, said interpositional admixture element includes a proximal facing tissue surface and a distal facing chamber surface, said plurality of surface gaps further ensure a passageway therebetween said proximal facing tissue surface and said distal facing chamber surface of said interpositional admixture element, said surface gaps are distributed throughtout said distal portion and said peripheral portion, said interpositional admixture element is operationally interposed therebetween said detachable closure cap, said internal surface and said closed distal end so as to ensure that the collection of bone growth elements strike an area of contact along a surface plane of said peripheral portion, said interpositional admixture element is further interposed so as to establish a tissue chamber proximally and an air chamber functionally thereabout said detachable closure cap, said interpositional admixture element is of a shape and dimension to ensure a vacuum path of least resistance, said vacuum path of least resistance comprising said tissue chamber, said plurality of surface gaps and said air chamber, said interpositional admixture element is further of a shape and dimension so as to induce a gravitional flow of the collection of bone growth elements along said surface plane, the gravitational flow is of a magnitude to induce mixing of components of the collection of bone growth elements; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

6. A tissue collection apparatus as described in claim 5 wherein said proximal extent further includes a securing member in operational relationship therewith for detachably engaging said proximal surface.

7. A tissue collection apparatus comprising:

a substantially cylindrical body having an open proximal end, an internal surface, a proximal surface and a closed distal end, said substantially cylindrical body further includes a detachable closure cap having a first portion of a size and shape adapted to receive a first connection tube, said detachable closure cap is of a shape and dimension to seal hermetically said open proximal end so as to prevent the retrograde flow of air at the jucture thereof and said substantially cylindrical body, said first portion includes a first internal passage for allowing a collection of bone growth elements substantially having platelets, mesenchymal cells, bone cells, blood and tissue cells, collagen and noncollagenous proteins comprising components thereof to flow through said first connection tube, said first internal passage and into said substantially cylindrical body, the collection of bone growth elements includes a proximal tissue surface and a peripheral tissue margin;

platelet aggregation surface means for inducing a quantity platelets within the collection of bone growth elements to adhere to an interpositional admixture element and degranulate thereon, said platelet aggregation surface means comprising a plurality of surface gaps, said interpositional admixture element includes a proximal extent and a distal portion adapted to receive the collection of bone growth elements and define a peripheral portion at the juncture thereof and said proximal extent, said interpositional admixture element includes a proximal facing tissue surface and a distal facing chamber surface, said plurality of surface gaps further ensure a passageway therebetween said proximal facing tissue surface and said distal facing chamber surface of said interpositional admixture element, said surface gaps are distributed throughout said distal portion and said peripheral portion, said interpositional admixture element is operationally interposed therebetween said detachable closure cap, said internal surface and said closed distal end so as to ensure that the collection of bone growth elements strike an area of contact along a surface plane of said peripheral portion, said interpositional admixture element is further interposed so as to establish a tissue chamber proximally and an air chamber distally within said substantially cylindrical body, said interpositional admixture element is of a shape and dimension to ensure a vacuum path of least resistance, said vacuum path of least resistance comprising said tissue chamber, said plurality of surface gaps and said air chamber, said interpositional admixture element is further of a shape and dimension so as to induce a gravitational flow of the collection of bone growth elements along said surface plane, the gravitational flow is of a magnitude to induce mixing of components of the collection of bone growth elements; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

8. A tissue collection apparatus as described in claim 7 wherein said proximal extent further includes a securing member in operational relationship therewith for detachably engaging said proximal surface.

9. A tissue collection apparatus comprising:

a substantially cylindrical body having an open proximal end, an internal surface, a proximal surface and a closed distal end, said substantially cylindrical body further includes a detachable closure cap having a first portion of a size and shape adapted to receive a first connection tube, said detachable closure cap is of a shape and dimension to seal hermetically said open proximal end so as to prevent the retrograde flow of air at the juncture thereof and said substantially cylindrical body, said first portion includes a first internal passage for allowing a collection of bone growth elements substantially having platelets, mesenchymal cells, bone cells, blood and tissue cells, collagen and noncollagenous proteins comprising components thereof to flow through said first connection tube, said first internal passage and into said substantially cylindrical body, the collection of bone growth elements includes a proximal tissue surface and a peripheral tissue margin;

surface means for inducing platelets within the collection of bone growth elements to degranulate ex vivo, said surface means comprising an interpositional admixture element having a plurality of surface gaps, said interpositional admixture element includes a proximal extent and a distal portion adapted to receive the collection of bone growth elements and define a peripheral portion a the juncture thereof and said proximal extent, said interpositional admixture element is operationally interposed therebetween said detachable closure cap, said internal surface and said closed distal end so as to ensure that the collection of bone growth elements strike an area of contact along a surface plane of said peripheral portion, said interpositional admixture element is further interposed so as to establish a tissue chamber proximally and an air chamber distally within said substantially cylindrical body, said interpositional admixture element is of a shape and dimension to ensure a vacuum path of least resistance; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

10. A tissue collection apparatus as defined in claim 9 wherein said interpositional admixture element further includes a proximal facing tissue surface and a distal facing chamber surface, said plurality of surface gaps further ensure a passageway therebetween said proximal facing tissue surface and said distal facing chamber surface of said interpositional admixture element.

11. A tissue collection apparatus as defined in claim 9 wherein said interpositional admixture element is further of a shape and dimension so as to induce a gravitational flow of the collection of bone growth elements along said surface plane, the gravitational flow is of a magnitude to induce mixing of components of the collection of bone growth elements.

12. A tissue collection apparatus as defined in claim 9 wherein said proximal extent further includes a securing member in operational relationship therewith for detachably engaging said proximal surface.

13. A tissue collection apparatus comprising:

a substantially cylindrical body having an open proximal end, an internal surface, a proximal surface and a closed distal end, said substantially cylindrical body further includes a detachable closure cap having a first portion of a size and shape adapted to receive a first connection tube, said detachable closure cap is of a shape and dimension to seal hermetically said open proximal end so as to prevent the retrograde flow of air at the juncture thereof and said substantially cylindrical body, said first portion includes a first internal passage for allowing a collection of bone growth elements substantially having platelets, mesenchymal cells, bone cells, blood and tissue cells, collagen and noncollagenous proteins comprising components thereof to flow through said first connection tube, said first internal passage and into said substantially cylindrical body, the collection of bone growth elements includes a proximal tissue surface and a peripheral tissue margin;

means for aggregating and inducing degranulation of the quantity of platelets within the collection of bone growth elements, said means comprising an interpositional admixture element includes a proximal extent and a distal portion adapted to receive the collection of bone growth elements and define a peripheral portion at the junction thereof and said proximal extent, said interpositional admixture element includes a proximal facing tissue surface and a distal facing chamber surface, said plurality of surface gaps further ensure a passageway therebetween said proximal facing tissue surface and said distal facing chamber surface of said interpositional admixture element, said surface gaps are distributed throughout said distal portion and said peripheral portion, said interpositional admixture element is operationally interposed therebetween said detachable closure cap, said internal surface and said closed distal end so as to ensure that the collection of bone growth elements strike an area of contact along a surface plane of said peripheral portion, said interpositional admixture element is further interposed so as to establish a tissue chamber proximally and an air chamber distally within said substantially cylindrical body, said interpositional admixture element is of a shape and dimension to ensure a vacuum path of least resistance, said interpositional admixture element is further of a shape and dimension so as to induce a gravitational flow of the collection of bone growth elements along said surface plane, the gravitational flow is of a magnitude to induce mixing of components of the collection of bone growth elements; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

14. A tissue collection apparatus as defined in claim 13 wherein said proximal extend further includes a securing member in operational relationship therewith for detachably engaging said proximal surface.

15. A tissue collection apparatus comprising:

a substantially cylindrical body having an open proximal end, an internal surface, a proximal surface and a closed distal end, said substantially cylindrical body further includes a detachable sealing cap, said detachable sealing cap is of a shape and dimension to seal hermetically said open proximal end so as to prevent the flow of air at the juncture thereof and said substantially cylindrical body, said detachable sealing cap includes a first portion having a first internal passage, said first internal passage is of a dimension for allowing a collection of bone growth elements substantially having a quantity of platelets, mesenchymal cells, bone cells, blood and tissue cells, collagen and noncollagenous proteins as components thereof to flow therethrough, said first portion is of a size and shape adapted to receive a first connection tube, the collection of bone growth elements includes a proximal tissue surface and a peripheral tissue margin;

procoagulant surface means interposed therebetween said first portion and said second portion for inducing the quantity of platelets within the collection of bone growth elements to degranualte, said procoagulant surface means comprising an interpositional admixture element, said interpositional admixture element includes a proximal extent and a distal portion adapted to receive the collection of bone growth elements and define a peripheral portion having a surface plane at the juncture thereof and said proximal extent, said interpositional admixture element includes a proximal facing tissue surface and a distal facing chamber surface, said interpositional admixture element further includes means for initiating bone formation therewithin the collection of bone growth elements, said means for initiating bone formation comprising a plurality of surface gaps having a size adapted to induce clot formation therewithin the collection of bone growth elements, said plurality of surface gaps further ensure a passageway therebetween said proximal facing tissue surface and said distal facing chamber surface of said interpositional admixture element, said interpositional admixture element is operationally interposed therebetween said detachable closure cap, said internal surface and said closed distal end so as to ensure that the collection of bone growth elements strike said procoagulant surface means along said surface plane of said peripheral portion, said interpositional admixture element is further interposed so as to establish a tissue chamber proximally and an air chamber distally within said substantially cylindrical body, said interpositional admixture element is of a shape and dimension to ensure a vacuum path of least resistance, said interpositional admixture element is further of a size and dimension so as to induce a gravitational flow of the collection of bone growth elements along said surface plane, said gravitational flow is of a magnitude to induce mixing of components of the collection of bone growth elements; and a second portion operationally disposed thereabout said substantially cylindrical body, said second portion is of a size and shape adapted for mounting vacuum means, said vacuum means inducing a flow of air through said vacuum path of least resistance, said vacuum means comprising a second connection tube, said second portion includes a second internal passage for allowing a flow of air therethrough.

16. A tissue collection apparatus as described in claim 15 wherein said proximal extent further includes a securing member in operational relationship therewith for detachably engaging said proximal surface.

* * * * *